United States Patent [19]

Nanjo et al.

[11] Patent Number: 5,742,374
[45] Date of Patent: Apr. 21, 1998

[54] FUNDUS CAMERA

[75] Inventors: Tsuguo Nanjo, Toyohashi; Masunori Kawamura, Nagoya, both of Japan

[73] Assignee: Nidek Company, Ltd., Japan

[21] Appl. No.: 791,345

[22] Filed: Jan. 31, 1997

[30] Foreign Application Priority Data

Jan. 31, 1996 [JP] Japan ................................ 8-038973

[51] Int. Cl.$^6$ .................................. A61B 3/14; A61B 3/10
[52] U.S. Cl. .......................... 351/206; 351/221; 354/62
[58] Field of Search .................... 351/206, 205, 351/211, 221, 200, 246; 354/62

[56] References Cited

U.S. PATENT DOCUMENTS

| | | | |
|---|---|---|---|
| 4,196,979 | 4/1980 | Kohayakawa et al. | 351/7 |
| 4,253,743 | 3/1981 | Matsummura | 351/7 |
| 5,048,946 | 9/1991 | Sklar et al. | 351/206 |
| 5,141,303 | 8/1992 | Yamamoto et al. | 351/211 |
| 5,240,006 | 8/1993 | Fujii et al. | 128/665 |
| 5,308,919 | 5/1994 | Minnich | 128/633 |
| 5,341,180 | 8/1994 | Isogai et al. | 351/206 |
| 5,543,865 | 8/1996 | Nanjo | 351/206 |

FOREIGN PATENT DOCUMENTS 56-63329   5/1981   Japan .

*Primary Examiner*—Hung X. Dang
*Attorney, Agent, or Firm*—Rossi & Associates

[57] ABSTRACT

A fundus camera for photographing fundus of an eye to be examined, comprises observing illumination/target projection optical system provided with a slit-plate having a pin-hole aperture and a ring-slit, for illuminating the eye to be examined with an illumination light bundle for use in observation that is formed by the ring-slit to be ring-shaped by illuminating the slit-plate uniformly, and for projecting an alignment index onto a cornea of the eye to be examined by using a light bundle that has passed through the pin-hole aperture, photographing illumination optical system for illuminating the eye to be examined with a ring-shaped illumination light bundle for use in photography by using a part of optical path of the observing illumination/target projection optical system, observation optical system for observing the focused condition of an image of the alignment index projected onto the cornea of the eye to be examined and the fundus of the eye to be examined by using the observing illumination/target projection optical system, and photographing optical system using a part of optical path of the observation optical system and for photographing the fundus of the eye to be examined that is illuminated with the photographing illumination optical system, whereby the suitability of the alignment is determined by observing the focused condition of the image of the alignment index by using the observation optical system.

14 Claims, 5 Drawing Sheets

FUNDUS CAMERA

BACKGROUND OF THE INVENTION

1. Field of the Invention

The present invention relates to a fundus camera for photographing fundus of an eye to be examined, and more particularly to a handheld apparatus for funduscopic photoimaging, particularly suitable for lying patients, baby and children, animals, handicapped persons and the like.

2. Description of Related Art

A fundus camera for photographing fundus of the eye to be examined needs a fine tune of positional relationship between the eye to be examined and the fundus camera, especially an adjustment of working distance is important.

In the case that the working distance is decide by using the usual handheld type of fundus camera, the relative position of the camera is determined in a manner that at first an anterior portion of the eye to be examined is observed from the side direction of the camera with focusing an illumination light bundle onto the anterior portion of the eye to be examined, and then it is confirmed that the illumination light bundle is focused onto an approximate predetermined position. Next, a fundus image of the eye is observed by looking through a finder by an eyepiece with maintaining its positional relationship as much as possible. Based on this observation, the detail alignment-adjustment such as elimination of flare caused by the illumination light, determination of photographing parts, bringing the fundus image into focus and the like are performed, after that photographing is performed.

However, such above-mentioned adjustment that the working distance is adjusted by observing from the side direction of the camera and then further precise alignment is performed with maintaining its positional relationship is unstable photographing method to some extent as a handheld type apparatus, therefore great deal of skill is required for photographing.

Also, in the case that an invisible infrared light is tried to be adopted as an observation-illumination light in order to perform non-mydriasis photography, the state of the illumination light bundle can not be observed from the side direction of the camera with operator's eye.

Furthermore, to install and dispose a flash light source for use in photography into a small handheld type enclosure is likely to cause difficulties, and also miniaturization and lightening weight are limited.

SUMMARY OF THE INVENTION

The present invention has been made in view of the above circumstances and has an object to overcome the above problems and to provide an fundus camera, capable of confirming the suitability of the working distance and an optical axis easily without any skilled experience concerning to deal with the fundus camera.

Another object of the present invention is to provide the fundus camera, capable of achieving to simplify and lighten a photographing unit corresponding to a handheld type enclosure.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a fundus camera for photographing fundus of an eye to be examined, comprises observing illumination/target projection optical system provided with a slit-plate having a pin-hole aperture and a ring-slit, for illuminating the eye to be examined with an illumination light bundle for use in observation that is formed by the ring-slit to be ring-shaped by illuminating the slit-plate uniformly, and for projecting an alignment index onto a cornea of the eye to be examined by using a light bundle that has passed through the pin-hole aperture, photographing illumination optical system for illuminating the eye to be examined with a ring-shaped illumination light bundle for use in photography by using a part of optical path of the observing illumination/target projection optical system, observation optical system for observing the focused condition of an image of the alignment index projected onto the cornea of the eye to be examined and the fundus of the eye to be examined by using the observing illumination/target projection optical system, and photographing optical system using a part of optical path of the observation optical system and for photographing the fundus of the eye to be examined that is illuminated with the photographing illumination optical system, whereby the suitability of the alignment is determined by observing the focused condition of the image of the alignment index by using the observation optical system.

In another aspect of the present invention, the fundus camera for photographing fundus of an eye to be examined, comprises observing illumination/target projection optical system provided with a slit-plate having a ring-slit and an aperture which forms an alignment target at a center area of the ring-slit, for illuminating the fundus of the eye to be examined by projecting an illumination light bundle within a range of the infrared-rays that is formed by said ring-slit, and for forming the alignment index by projecting the illumination light bundle that has passed through the aperture, photographing illumination optical system including a optical path synthesizing means for aligning coaxially with said photographing illumination optical system and a shutting means disposed at a conjugate position relative to the slit-plate for shutting the visible light passing through the aperture, and for illuminating the fundus of the eye to be examined by projecting the visible light that are formed by the ring-slit onto the eye to be examined, observation optical system for observing the fundus of the eye to be examined and the alignment index by using the illumination light bundle within a range of the infrared-rays, and photographing optical system for photographing the fundus of the eye to be examined by using the visible light passing through a optical path which is branched by optical path branching means disposed in the observation optical system.

In another aspect of the present invention, the fundus camera including a photographing unit, a control unit, and plasticizing optical fiber cables for connecting the photographing unit and the control unit optically for photographing fundus of an eye to be examined, comprises observing illumination/target projection optical system disposed in the photographing unit, for illuminating the eye to be examined with the infrared-rays and for projecting an alignment target onto a cornea of the eye to be examined, a slit-plate disposed in the observing illumination/target projection optical system, having a pin-hole aperture for projecting a passed light bundle corresponding to the infrared-rays as the alignment index onto the cornea of the eye to be examined as well as a ring-slit for projecting a passed light bundle corresponding to the infrared-rays as an illumination light bundle for use in observation onto the eye to be examined, a light source for use in photography and illumination that is disposed in the control part, for illuminating the eye to be examined with the visible light, shutting means disposed at an emerging end-plane of optical fiber cables for delivering the visible light emitted from a light source for use in photography and illumination, for shutting the slit-plate so that the visible light delivered from the photographing illumination optical system may pass the ring-slit of the slit-plate while prohibiting from passing through the pin-hole aperture, and observation/photography optical system disposed in the photographing unit, for observing the fundus of the eye to be examined and the focused condition of the image of the alignment index with the infrared-rays of the observing illumination/target projection optical system, and for photographing the fundus of the eye to be examined by using the visible light of the photographing illumination optical system.

According to the present invention, the apparatus enables to perform confirmation and alignment of the suitability of the working distance and the optical axis easily without requiring for particular skilled experience concerning to deal with a fundus camera.

In addition, since a flash light source for use in photography is separated from the photographing unit, and an illumination light bundle emitted from a light source is made to be delivered to the photographing unit through optical fibers, it is capable of simplifying and lightening the photographing unit so as to be particularly suitable for handheld type enclosure.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawing, FIG. 1. is a view showing a schematic construction of a fundus camera of the preferred embodiment.

DETAILED DESCRIPTION OF THE PREFERRED EMBODIMENTS

A detailed description of one preferred embodiment of a fundus camera embodying the present invention will now be given referring to the accompanying drawing.

Figure 1:
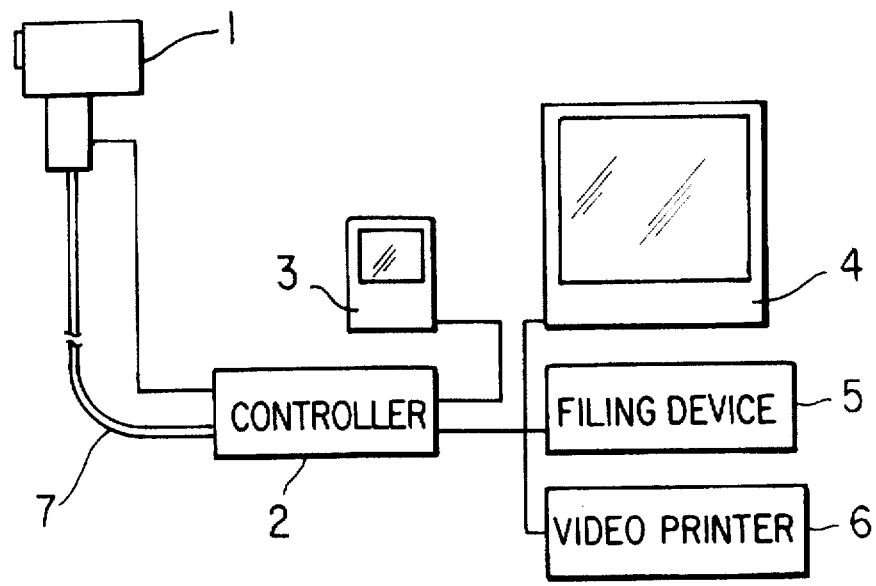

FIG. 1 is a schematic construction of a fundus camera of the preferred embodiment. The fundus camera of the preferred embodiment consists of a photographing unit 1 which has the optical system and the like for observation and photography in a enclosure suitable for handheld operation, a controller 2 for controlling the photographing unit 1 that has a flash light source for use in photography, an observation monitor 3, a display monitor 4, a filing device 5 and a video printer 6, and respective parts are connected electrically. Also, the illumination light emitted from the flash light source for use in photography of the controller 2 is delivered to the optical system inside the photographing unit 1 passing through a optical fiber bundle 7.

Figure 2:
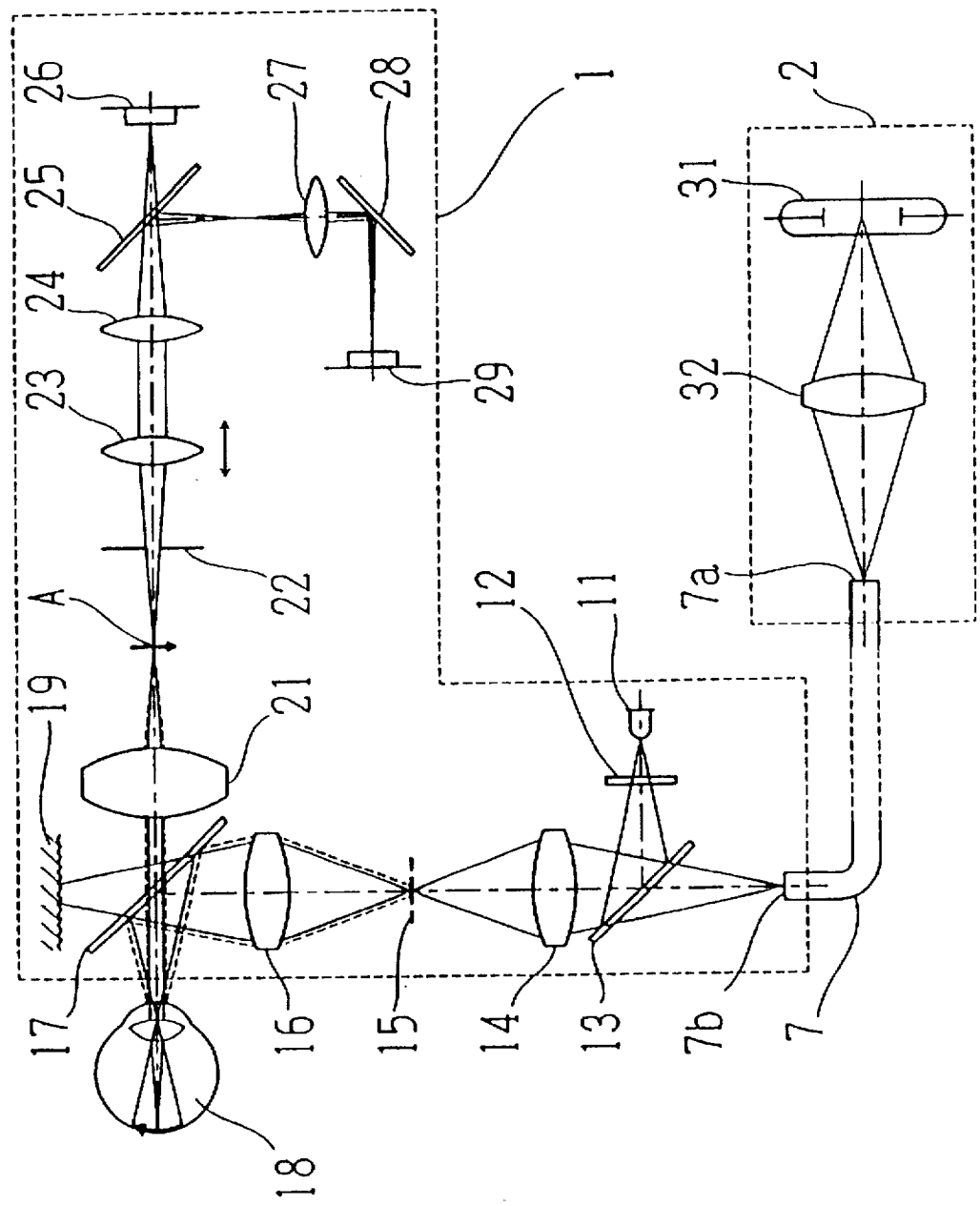
FIG. 2 is a view showing a detailed construction of optical system of the fundus camera of the preferred embodiment.

FIG. 2 is a view showing the optical system of the fundus camera. The optical system will be described hereinafter by dividing into the observing illumination/target projection optical system, the photographing illumination optical system, and the observation/photographing optical system separately. (The illumination for observing/target projection optical system)

Figure 3:
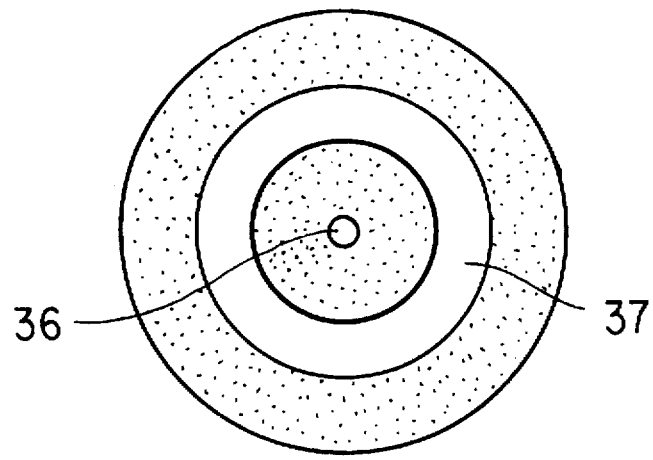
FIG. 3 is a view showing a pin-hole aperture and a ring-slit included in a slit-plate of the fundus camera of the preferred embodiment.

Reference numeral 11 denotes an infrared light emitting diode which is the illumination light source for use in observation, the infrared light emitting diode 11 is also used as a target projection light source for alignment. Reference numeral 12 denotes a diffusion plate, reference numeral 13 denotes a dichroic mirror which has such characteristics that reflects the infrared light and that transmits the visible light for use in photography. Reference numeral 14 denotes a condenser lens, reference numeral 15 denotes a slit-plate which has a pin-hole aperture 36 at the center thereof and a ring-slit aperture 37 around the optical axis as shown in FIG. 3. Reference numeral 16 denotes a projective lens, reference numeral 17 denotes a beam splitter which makes an optical axis of the illumination/target projection system be coaxial with an optical axis of the observation/photographing optical system that mentioned below. Reference numeral 19 denotes a black absorber for absorbing the illumination light bundle having transmitted through the beam splitter 17 in order to prevent noise light unnecessary for use in the observation/photographing optical system from entering. Reference numeral 18 denotes an eye to be examined.

The infrared light bundle emitted from the infrared light emitting diode 11 is unified by the diffusion plate 12, and then the infrared light bundle is reflected by the dichroic mirror 13, and is focused by the condenser lens 14 so that whole of the pin-hole aperture 36 and the ring-slit aperture 37 on the slit-plane 15 may be illuminated.

The light bundle passed through from the pin-hole aperture 36 and the ring-slit aperture 37 enters into the beam splitter 17 passing through the projective lens 16, of which the quantity of light is attenuated to approximate ½ at the time when the light bundle is reflected, and then the light bundle is delivered to the eye 18 to be examined. When the photographing unit 1 is placed at the position of a predetermined working distance, the light bundle which is limited to be ringed-shape by the ring-slit aperture 37, is diffused after an image of the ring-slit aperture 37 is once formed on an area close to the pupil of the eye 18, so that the fundus of the same size as a field of vision is taken a photograph or of the larger size thereof to some extent is illuminated by an invisible infrared light.

An alignment light bundle passed through the pin-hole aperture 36, as well as the ring light bundle, are focused at the anterior portion of the eye to be examined, and when the photographing unit 1 is placed at the position of approximate predetermined working distance, an image of the alignment target is formed as if they were focused within approximate half of the radius of corneal curvature from the surface of cornea by the reflection of cornea. However, since the light bundle formed by the pin-hole aperture 36 is a light bundle close to the optical axis different from the ring light bundle by the ring-slit aperture 37, therefore in the case that a reflected light from the cornea is appropriate working distance, it changes to a parallel light bundle and is delivered to the observation/photographing optical system that mentioned below.

Still, the infrared light bundle which has been attenuated and transmitted through the beam splitter 17 is absorbed by the black absorber 19 without reflecting. (Photographing illumination optical system)

Reference numeral 31 denotes a flash light source for use in photography, reference numeral 32 denotes a condenser lens. The flash light source 31 and the condenser lens 32 are disposed in the controller 2, and the illumination light bundle for use in photography transmitted from the controller 2 is delivered to the photographing unit 1 through the optical fiber bundle 7. The photographing illumination optical system in the photographing unit 1 shares the same optical path from the dichroic mirror 13 through the beam splitter 17 in the observing illumination/target projection optical system.

Figure 5:
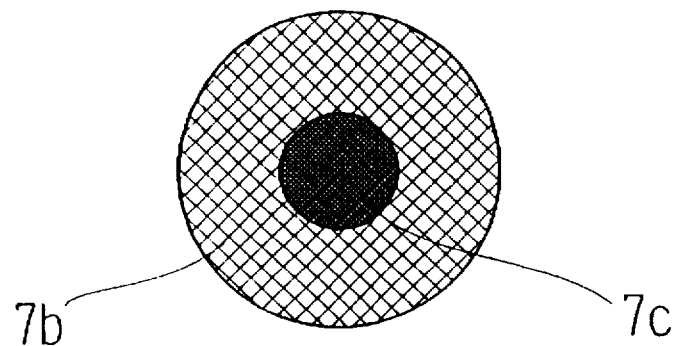
FIG. 5 is a view showing a shutting element 7c and an emerging end-plane 7b of the optical fiber bundle 7.

There is an shutting element 7c at the center of an emerging end-plane 7b of the optical fiber bundle 7 (shown in FIG. 5). The emerging end-plane 7b of the optical fiber bundle 7 is disposed at the conjugate position relative to the slit-plate 15 through the condenser lens 14.

The visible illumination light for use in photography which has emitted from the flash light source 31 is focused by the condenser lens 32, then whole of the entering end-plane 7a of the optical fiber bundle 7 is illuminated completely. Thereby, the illumination light delivered to the optical fiber bundle 7 is formed to a surface emitting light at the emerging end-plane 7b, and further it is formed to a ring-shaped light bundle caused by the intercepting part of the center part of the emerging end-plane 7b. After the ring-shaped light bundle from the emerging end-plane 7b is transmitted through the dichroic mirror 13, then it illuminates the slit-plate 15 passing through the condenser lens 14. Since the slit-plate 15 is conjugate with the emerging end-plane 7b of the optical fiber bundle 7, the light bundle which is formed to be the ring-shaped illuminates only the ring-slit aperture 37 without illuminating the pin-hole aperture 36 of the slit-plate 15. That is, it is equivalent to be equipped with the second slit-plate.

The illumination light bundle for use in photography which is formed to be the ring-shaped by the ring-slit aperture 37 is delivered to the eye to be examined, passed through the same optical path as the illumination light bundle for observation, and it illuminates the fundus of the eye to be examined.

(Observing/Photographing Optical System)

Reference numeral 21 denotes an objective lens for use in observation, reference numeral 22 denotes a photographing diaphragm which is disposed at the conjugate position relative to the pupil of the eye 18 to be examined. Reference numeral 23 denotes a focusing lens capable of moving in the direction of optical axis by lens moving mechanism (not shown) in order to adjust in response to the refractive power of the eye to be examined. Reference numeral 24 denotes an image forming lens, reference numeral 25 denotes a dichroic mirror having such characteristics that it reflects the infrared light and transmits the visible light beam. Reference numeral 26 denotes a CCD camera for photographing. Since the sensitivity of the imaging element of this CCD camera 26 is enough to catch the lower quantity of light compared with the picture photography using 35 mm film, the quantity of light of the illumination bundle for use in photography can be controlled lower.

Reference numeral 27 denotes a relay lens for extending the optical path, reference numeral 28 denotes a mirror for reversing a mirror image, and reference numeral 29 denotes an infrared CCD camera for use in observation.

The fundus of eye to be examined is illuminated by a ring-shaped infrared illumination light delivered from the observing illumination/target projection optical system. The light reflected by the fundus by this illumination emerges from an area close to the optical axis that is not overlapped with the ring image by the ring-slit aperture 37. The light bundle emerged from the eye 18 to be examined is further attenuated to approximate ½ of the quantity of light by the beam splitter 17, after an inverted image is imaged on the point A by the objective lens 21, then it passes through the photographing diaphragm Since the photographing diaphragm 22 is conjugate with the pupil, therefore a diameter of photographic light bundle emerged from the pupil part of the eye 18 is determined by the photographing diaphragm 22 so as not to be overlapped with other ring image by an ring-slit aperture 37.

The light bundle within a range of infrared-ray having passed through the photographing diaphragm 22 is passed through the focusing lens 23 and the image forming lens 24, and is reflected by the dichroic mirror 25, then it is imaged on the imaging element of the infrared CCD camera 29 by the relay lens 27.

On the other hand, since the alignment index light bundle which is formed by the pin-hole aperture 36 and projected onto the eye 18 to be examined is a light bundle of the center part on the optical axis, so in the case that the photographing unit 1 is placed at an approximate predetermined working distance, the index light bundle reflected by specular reflection at the corneal vertex is changed to an approximate parallel light bundle, and is delivered to the objective lens 21. After that, the index light bundle is traced the optical path similar to the path of the reflected light bundle from the fundus, then is imaged on the imaging element of the infrared CCD camera 29. The image of the alignment index as well as the fundus image are displayed on the observation monitor 3.

Also, a visible light bundle reflected by the fundus which is illuminated by the photographing illumination optical system enters into the dichroic mirror 25 passing through the objective lens 21, the photographing diaphragm 22, the focusing lens 23 and the image forming lens 24 as the same as the reflected light bundle from the fundus by infrared light. Since the dichroic mirror 25 transmits the visible light bundle, so the visible light bundle reflected by the the fundus is imaged on the surface of the imaging element of the CCD camera 26 by the image forming lens 24. In the photographing illumination optical system, only the illumination light bundle with ring-shaped which is formed by the ring-slit aperture 37 is projected onto the eye to be examined without illuminating the pin-hole aperture 36, therefore the image of alignment index is not formed as the observing illumination/target projection optical system. As a result, the definite fundus image can be obtained by the CCD camera 26 for photographing. The fundus image photographed by the CCD camera 26 is displayed as captured image on the display monitor 4.

Figure 4:
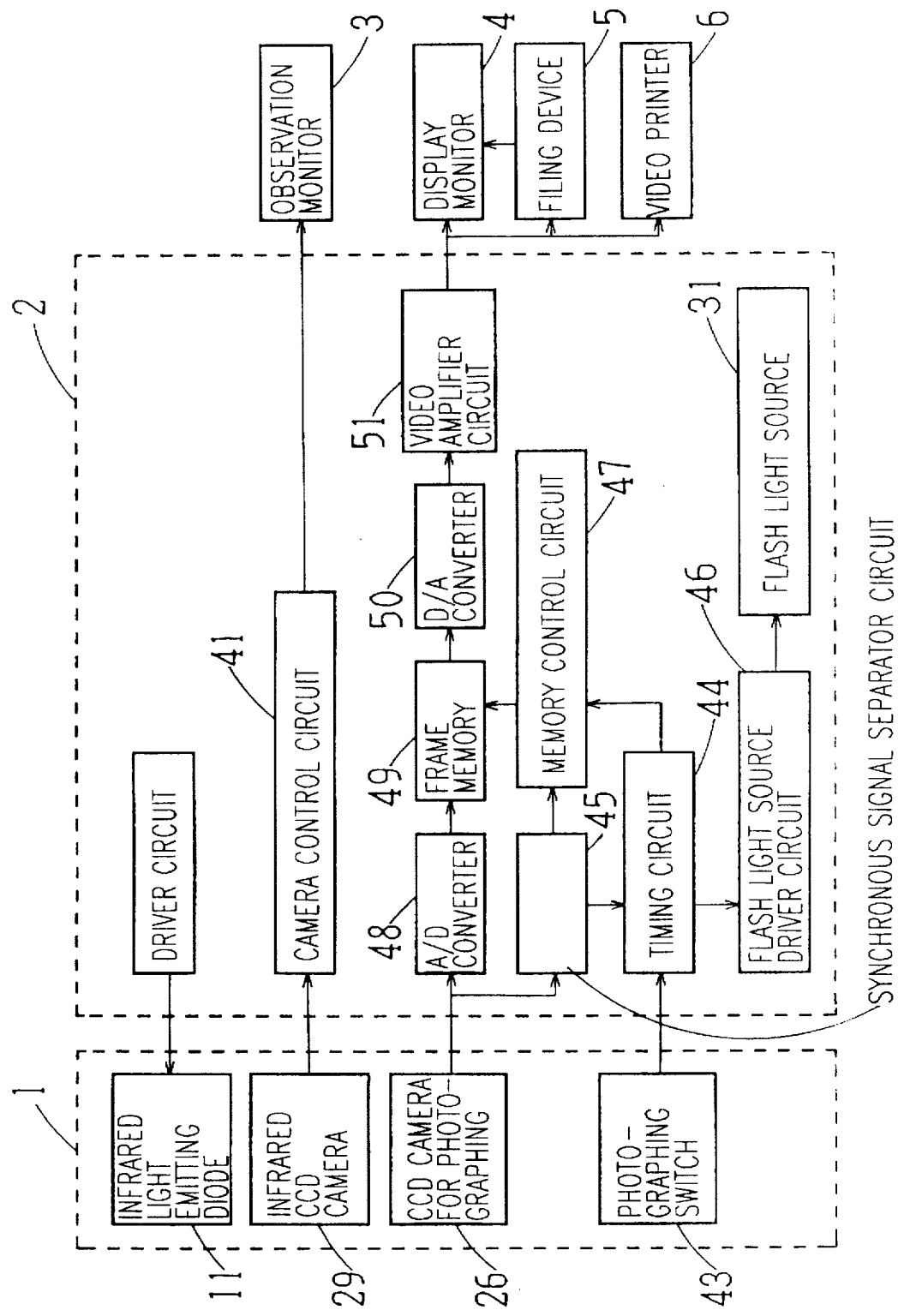
FIG. 4 is a block diagram showing a principal control system of the fundus camera of the preferred embodiment.

The operation of the apparatus having such architecture as described above will be described hereinafter with referring to the block diagram showing a principal control system as shown in FIG. 4.

As a photographing environment, the extent of brightness may be preferable in a level adequate for reading words in newspaper, and the extent of the pupil may be preferable that the pupil of the eye to be examined can be opened widely under the condition of the natural mydriasis. At first, the driving circuit is gone into run by operating a switch (not shown) equipped with the controller 2, thereby the infrared light emitting diode 11 is turned on. The operator holds the enclosure of the photographing unit 1, and makes the photographing unit 1 closer to the eye 18 to be examined from his side so as to illuminate the eye 18. The light bundle of the illumination for observing and the light bundle of the target projection are invisible infrared light bundles, therefore it is possible to illuminate the eye to be examined without making it feel dazzle.

The light reflected by the eye to be examined which is illuminated by the infrared light bundle is caught by the infrared CCD camera 29, and the photo-image is displayed on the observation monitor 3 through a camera control circuit 41. The image of the eye to be examined which is observed by the observation monitor 3 is begun to be illuminated from the operator's side to some extent, therefore the anterior portion of the eye to be examined is displayed at first. When the operator makes the apparatus closer to the position of the working distance of the fundus camera with observing its image, the image of the pupil comes to be widely spread in the observation monitor 3, and then the fundus image is displayed therein.

Upon this condition, the image of alignment index by the pin-hole aperture 36 is displayed simultaneously with the image of fundus on the observation monitor 3, thereby the operator can confirm it. Although this image of index is enlarged and blurred at first, in accordance with approaching to the appropriate working distance, it is focused and becomes smaller size gradually. While the operator adjusts the optical axis in order to make the image of index place at the center part of the display, furthermore he adjusts the working distance with maintaining the position of this image of index. When the image of index is brought into the best focus condition, the appropriate working distance can be obtained.

Under the condition of the appropriate working distance, when the image of fundus is blurred due to the refractive power of the eye to be examined, the focusing lens 23 should be moved so as to bring the fundus into focus. To bring the fundus image into focus may be performed based on well-known focusing index such as a split illuminant line and the like. As described above, the adjustment of the working distance can be achieved easily with observing the observation monitor 3.

Next, the operator makes a photographing part of the fundus move with defining the pupil as the center by swinging the photographing unit 1 with maintaining the position of the image of alignment index on the center of the display, so that the photographing part of the fundus may be determined in detail.

After the determination of the photographing part of the fundus has been completed, the operator presses the photographing switch 43 equipped with the photographing unit 1. When the photographing switch 43 is pressed, a timing circuit 44 of the controller 2 sends the operating signal to a flash light source driver circuit 46 and a memory control circuit 47 by making it synchronize with the synchronous signal delivered from the CCD camera 26 for photographing which is inputted through a synchronous signal separator circuit 45. When a flash light source 31 emits caused by driving the flash light source driver circuit 46, the fundus image illuminated in the photographing illumination optical system is caught by the CCD camera 26 for photographing. The image signal caught by the CCD camera 26 is converted to digital signal by an A/D converter 48, and the digital signal is stored into the frame memory 49 in a manner that its image signal is synchronized with a signal delivered from the memory control circuit 47.

The photo-image stored in the frame memory 49 is converted to an analog signal by a D/A converter 50, and then the analog signal is sent to the display monitor 4 through a video amplifier circuit 51 so as to be displayed thereon instantaneously. The operator confirms that whether the photographed fundus image displayed on the display monitor 4 is satisfactory or not. In the case that the photo-image is not satisfactory, the photographing condition such as the adjustment of the amount of the flash light source 31 and the like should be reset, then the photography should be performed once more by way of the same process.

In the case that the photo-image is stored, the photo-image should be stored by operating a filing device 5. The photo-image on the fundus image memorized and stored into the filing device 5 is retrievable, and the unnecessary photo-image may be deleted and edited. Furthermore, in the case that printed image is necessary for pasting in medical records and the like, it can be printed out by operating a video printer 6.

Still, although the observation monitor 3 is disposed separately from the photographing unit 1 in the preferred embodiment, if a miniature size of LCD (liquid crystal display) and the like is applied instead of the observation monitor 3 and is disposed in the photographing unit 1, then the operation performance would be much better.

Also, the observation monitor 3 and the display monitor may be provided with an image switching means, thereby the observation image and the photographing image can be displayed on the same monitor by sharing it.

The present invention may be embodied in other specific forms without departing from the spirit or essential characteristics thereof. For instance, in the photographing illumination optical system of the preferred embodiment, although the shutting element is provided at the center part of the emerging end-plane 7b of the optical fiber bundle 7, it is also possible that a shutting element for preventing the pin-hole aperture 36 from being illuminated is just disposed at a conjugate position corresponding to the slit-plate 15, and the flash light source is provided in the photographing unit 1 instead of the optical fiber bundle 7.

Figure 6:
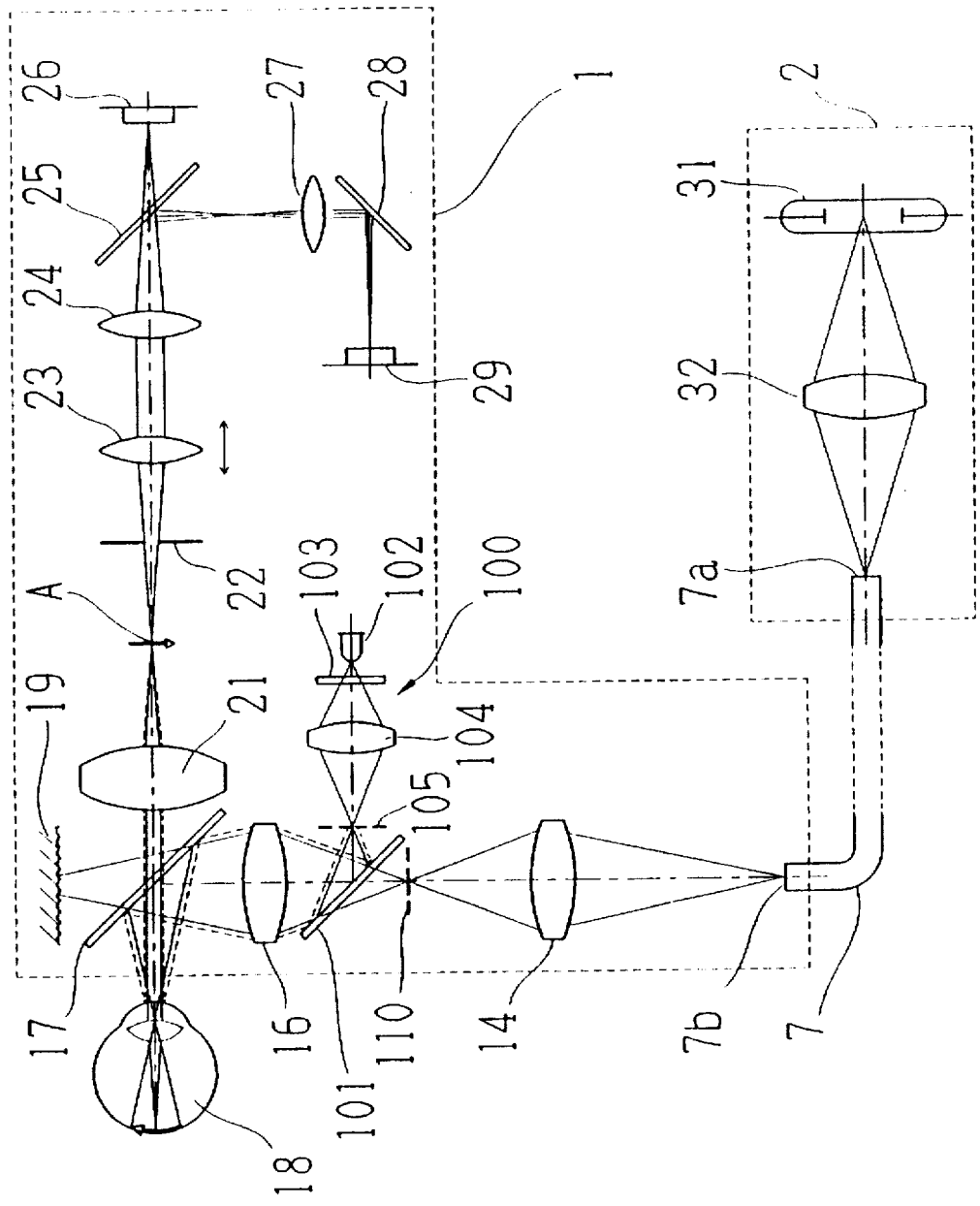
FIG. 6 is a view showing a detailed construction of optical system of the fundus camera of the second preferred embodiment.

Also, although the ring-slit aperture 37 of the slit-plate 15 is shared in order to produce the ring illumination light bundle for use in photography in the preferred embodiment, the ring-slit for use in observation and the ring-slit for use in photography can be separated. That is, as shown in FIG. 6, the optical path of the infrared light bundle in the observing illumination/target projection optical system projected by the projective lens 16 and the optical path of the visible light bundle in the photographing illumination optical system should be synthesized by a beam splitter 101. The first slit-plate 105 (same as the slit-plate 15) having a pin-hole aperture and ring-slit aperture is disposed at an exclusive optical path 100 of the observing illumination/target projection optical system as well as an infrared light source 102, a diffusion plate 103 and a condenser lens 104. The second slit-plate 110 having only the same ring-slit aperture as the first slit-plate 105 is disposed at an exclusive optical path of the photographing illumination optical system. Then, the first slit-plate 105 and the second slit-plate 110 are disposed at a conjugate position corresponding to the ring-slit image which is imaged by the projective lens 16. Thereby, both of projection of the alignment index and the illumination of the fundus can be achieved by way of the same method as the preffered embodiment.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. A fundus camera for photographing fundus of an eye to be examined, comprising:

observing illumination/target projection optical system provided with a slit-plate having a pin-hole aperture and a ring-slit, for illuminating the eye to be examined with an illumination light bundle for use in observation that is formed by said ring-slit to be ring-shaped by illuminating said slit-plate uniformly, and for projecting an alignment index onto a cornea of the eye to be examined by using a light bundle that has passed through said pin-hole aperture;

photographing illumination optical system for illuminating the eye to be examined with a ring-shaped illumination light bundle for use in photography by using a part of optical path of said observing illumination/ target projection optical system;

observation optical system for observing the focused condition of an image of the alignment index projected onto the cornea of the eye to be examined and the fundus of the eye to be examined by using said observing illumination/target projection optical system; and photographing optical system using a part of optical path of said observation optical system and for photographing the fundus of the eye to be examined that is illuminated with said photographing illumination optical system, whereby the suitability of the alignment is determined by observing the focused condition of the image of the alignment index by using said observation optical system.

2. A fundus camera according to claim 1, further comprising:

a beam splitter disposed along with the optical path shared by said observation optical system and said photographing illumination optical system, for reflecting said illumination light bundle for use in observation, said light bundle for use in target projection, and said light bundle for use in photography into the eye to be examined.

3. A fundus camera according to claim 1, wherein said photographing illumination optical system forms a ring-shaped illumination light bundle by illuminating only the ring-slit of said slit-plate.

4. A fundus camera according to claim 3, wherein said photographing illumination optical system comprises shutting means disposed at a light source side corresponding to a conjugate position relative to said slit-plate, for prohibiting the light bundle from passing through said pin-hole aperture.

5. A fundus camera according to claim 1, wherein said photographing illumination optical system includes a second slit-plate for making the light bundle for use in photography to be approximate the same illumination light bundle as the ring-shaped illumination light bundle delivered from said observing illumination/target projection optical system.

6. A fundus camera according to claim 1, wherein the pin-hole aperture of said slit-plate is disposed on the optical axis of said observing illumination/target projection optical system.

7. A fundus camera according to claim 1, wherein said observing illumination/target projection optical system includes a light source for illuminating said slit-plate with the infrared-rays, and said observation optical system includes a photoelectric imaging elements having sensitivity in the infrared-range and displaying means for displaying an image created by said photoelectric imaging elements.

8. A fundus camera according to claim 1, further comprising a handheld type enclosure, wherein a light source of the said photographing illumination optical system is separated from said handheld type enclosure, and an illumination light for use in photography emitted from said light source is delivered by optical fibers.

9. A fundus camera according to claim 8, wherein an emerging end-plane of said optical fibers is disposed at a conjugate position relative to said slit-plate, and a center part of the emerging end-plane is intercepted.

10. A fundus camera for photographing fundus of an eye to be examined, comprising:

observing illumination/target projection optical system provided with a slit-plate having a ring-slit and an aperture which forms an alignment target at a center area of the ring-slit, for illuminating the fundus of the eye to be examined by projecting an illumination light bundle within a range of the infrared-rays that is formed by said ring-slit, and for forming the alignment index by projecting the illumination light bundle that has passed through said aperture;

photographing illumination optical system including a optical path synthesizing means for aligning coaxially with said photographing illumination optical system and a shutting means disposed at a conjugate position relative to said slit-plate for shutting the visible light passing through said aperture, and for illuminating the fundus of the eye to be examined by projecting the visible light that are formed by the ring-slit onto the eye to be examined;

observation optical system for observing the fundus of the eye to be examined and the alignment index by using said illumination light bundle within a range of the infrared-rays; and photographing optical system for photographing the fundus of the eye to be examined by using the visible light passing through a optical path which is branched by optical path branching means disposed in said observation optical system.

11. A fundus camera according to claim 10, wherein said optical path synthesizing means consists of a beam splitter for reflecting the one light bundle and for transmitting another light bundle between said photographing illumination optical system and said observing illuminating/target projection optical system in order to deliver both of light bundles onto the eye to be examined.

12. A fundus camera according to claim 10, wherein said shutting means is disposed at a conjugate position relative to both of said slit-plate and a condenser lens for illuminating said slit-plate.

13. A fundus camera according to claim 10, wherein said optical path branching means consists of a dichroic mirror for reflecting the one light bundle and for transmitting another light bundle between the infrared-rays and the visible -rays that pass through said observation optical system and said photographing optical system.

14. A fundus camera including a photographing unit, a control unit, and plasticizing optical fiber cables for connecting said photographing unit and said control unit optically for photographing fundus of an eye to be examined, comprising:

observing illumination/target projecting optical system disposed in said photographing unit, for illuminating the eye to be examined with the infrared-rays and for projecting an alignment target onto a cornea of the eye to be examined;

a slit-plate disposed in said observing illumination/target projecting optical system, having a pin-hole aperture for projecting a passed light bundle corresponding to said infrared-rays as said alignment index onto the cornea of the eye to be examined as well as a ring-slit for projecting a passed light bundle corresponding to said infrared-rays as an illumination light bundle for use in observation onto the eye to be examined;

a light source for use in photography and illumination that is disposed in said control part, for illuminating the eye to be examined with the visible light;

shutting means disposed at an emerging end-plane of optical fiber cables for delivering the visible light emitted from a light source for use in photography and illumination, for shutting the slit-plate so that the visible light delivered from said photographing illumination optical system may pass the ring-slit of said slit-plate while prohibiting from passing through the pin-hole aperture; and observation/photography optical system disposed in said photographing unit, for observing the fundus of the eye to be examined and the focused condition of the image of the alignment index with the infrared-rays of said observing illumination/target projecting optical system, and for photographing the fundus of the eye to be examined by using the visible light of said photographing illumination optical system.

\* \* \* \* \*